(12) United States Patent
Wendlinger et al.

(10) Patent No.: US 11,028,027 B2
(45) Date of Patent: Jun. 8, 2021

(54) PROCESS FOR PRODUCING 2-CHLORO-3,3,3-TRIFLUOROPROPENE

(71) Applicant: Arkema France, Colombes (FR)

(72) Inventors: Laurent Wendlinger, Pierre-Benite (FR); Dominique Deur-Bert, Pierre-Benite (FR); Anne Pigamo, Pierre-Benite (FR)

(73) Assignee: ARKEMA FRANCE, Colombes (FR)

( * ) Notice: Subject to any disclaimer, the term of this patent is extended or adjusted under 35 U.S.C. 154(b) by 0 days.

(21) Appl. No.: 16/976,520

(22) PCT Filed: Mar. 4, 2019

(86) PCT No.: PCT/FR2019/050478
§ 371 (c)(1),
(2) Date: Aug. 28, 2020

(87) PCT Pub. No.: WO2019/170990
PCT Pub. Date: Sep. 12, 2019

(65) Prior Publication Data
US 2021/0002189 A1    Jan. 7, 2021

(30) Foreign Application Priority Data
Mar. 7, 2018  (FR) ..................... 1851955

(51) Int. Cl.
*C07C 17/20* (2006.01)
*C07C 17/25* (2006.01)
*C07C 21/18* (2006.01)

(52) U.S. Cl.
CPC .......... *C07C 17/206* (2013.01); *C07C 17/25* (2013.01); *C07C 21/18* (2013.01)

(58) Field of Classification Search
CPC ........ C07C 17/206; C07C 17/25; C07C 21/18
See application file for complete search history.

(56) References Cited

U.S. PATENT DOCUMENTS

| | | |
|---|---|---|
| 2,773,014 A | 12/1956 | Snuggs et al. |
| 4,902,838 A | 2/1990 | Manzer et al. |
| 5,227,350 A | 7/1993 | Scott et al. |
| 5,322,597 A | 6/1994 | Childs et al. |
| 5,334,784 A | 8/1994 | Blake et al. |
| 5,919,728 A | 7/1999 | Rinaldi et al. |
| 8,614,361 B2 | 12/2013 | Suzuki et al. |
| 8,618,338 B2 | 12/2013 | Elsheikh et al. |
| 9,255,045 B2 | 2/2016 | Pigamo et al. |
| 9,340,473 B2 | 5/2016 | Pigamo et al. |
| 9,708,234 B2 | 7/2017 | Chaki et al. |
| 9,834,499 B2 | 12/2017 | Pigamo et al. |
| 10,227,275 B2 | 3/2019 | Pigamo et al. |
| 10,427,998 B2 | 10/2019 | Pigamo et al. |
| 10,532,965 B2 | 1/2020 | Pigamo et al. |
| 2009/0240090 A1 | 9/2009 | Merkel et al. |
| 2009/0287026 A1 | 11/2009 | Kopkalli et al. |
| 2010/0191025 A1 | 7/2010 | Perdrieux |
| 2011/0031436 A1 | 2/2011 | Mahler et al. |
| 2013/0197281 A1 | 8/2013 | Hintzer et al. |
| 2013/0267740 A1* | 10/2013 | Wendlinger .......... C07C 17/383 570/156 |
| 2014/0012051 A1 | 1/2014 | Pigamo et al. |
| 2014/0039228 A1 | 2/2014 | Pigamo et al. |
| 2014/0275653 A1 | 9/2014 | Pigamo et al. |
| 2015/0008357 A1 | 1/2015 | Furuta et al. |
| 2015/0197467 A1 | 7/2015 | Pigamo et al. |
| 2016/0115104 A1 | 4/2016 | Pigamo et al. |
| 2016/0237009 A1 | 8/2016 | Deur-Bert et al. |
| 2017/0158586 A1 | 6/2017 | Collier et al. |
| 2017/0210686 A1 | 7/2017 | Pigamo et al. |
| 2018/0093934 A1 | 4/2018 | Pigamo et al. |
| 2018/0148394 A1 | 5/2018 | Pigamo et al. |
| 2019/0127303 A1 | 5/2019 | Ondrus et al. |
| 2019/0152883 A1 | 5/2019 | Pigamo et al. |
| 2019/0375698 A1 | 12/2019 | Pigamo et al. |

(Continued)

FOREIGN PATENT DOCUMENTS

| | | |
|---|---|---|
| CN | 107540011 A | 1/2018 |
| EP | 0 449 617 A2 | 10/1991 |
| EP | 0582192 A1 | 2/1994 |

(Continued)

OTHER PUBLICATIONS

Bonnet, "Liquid-phase HF Fluorination", Multiphase Homogeneous Catalysis, 5.2 State of the Art, 2002 (month unknown), pp. 535-542.
International Search Report (PCT/ISA/210) dated Jun. 6, 2019, by the French Patent Office as the International Searching Authority for International Application No. PCT/FR2019/050479.
International Search Report (PCT/ISA/210) dated Jun. 19, 2019, by the European Patent Office as the International Searching Authority for International Application No. PCT/FR2019/050477.

(Continued)

*Primary Examiner* — Jafar F Parsa

(74) *Attorney, Agent, or Firm* — Buchanan Ingersoll & Rooney P.C.

(57) ABSTRACT

The present invention relates to a process for the production of 2-chloro-3,3,3-trifluoropropene comprising the stages of:

a) providing a stream A comprising at least one of the compounds selected from the group consisting of 2,3-dichloro-1,1,1-trifluoropropane, 1,1,1,2,3-pentachloropropane, 1,1,2,3-tetrachloropropene and 2,3,3,3-tetrachloropropene;

b) in a reactor, bringing said stream A into contact with HF in the presence or absence of a catalyst in order to produce a stream B comprising 2-chloro-3,3,3-trifluoropropene; characterized in that the electrical conductivity of said stream A provided in stage a) is less than 15 mS/cm.

10 Claims, No Drawings

(56) References Cited

U.S. PATENT DOCUMENTS

2020/0407293 A1   12/2020   Wendlinger et al.
2021/0002188 A1   1/2021    Wendlinger et al.

FOREIGN PATENT DOCUMENTS

| | | |
|---|---|---|
| EP | 0 939 071 A1 | 9/1999 |
| FR | 3 013 606 | 5/2015 |
| WO | 0181353 A1 | 11/2001 |
| WO | 2007079431 A2 | 7/2007 |
| WO | WO 2008/040969 A2 | 4/2008 |
| WO | WO 2008/054781 A1 | 5/2008 |
| WO | 2008149011 A2 | 12/2008 |
| WO | WO 2009/118628 A1 | 10/2009 |
| WO | 2009137658 A2 | 11/2009 |
| WO | 2011077192 A1 | 6/2011 |
| WO | 2012012113 A1 | 1/2012 |
| WO | 2012052797 A1 | 4/2012 |
| WO | WO 2012/098421 A1 | 7/2012 |
| WO | WO 2012/098422 A1 | 7/2012 |
| WO | 2013088195 A1 | 6/2013 |
| WO | WO 2013/154059 A1 | 10/2013 |
| WO | WO 2013/182816 A1 | 12/2013 |
| WO | WO 2014/010750 A1 | 1/2014 |
| WO | 2017178857 A1 | 10/2017 |

OTHER PUBLICATIONS

Written Opinion (PCT/ISA/237) dated Jun. 6, 2019, by the French Patent Office as the International Searching Authority for International Application No. PCT/FR2019/050479.

Written Opinion (PCT/ISA/237) dated Jun. 19, 2019, by the European Patent Office as the International Searching Authority for International Application No. PCT/FR2019/050477.

Mukerjee, et al., "Effect of Temperature on the Electrical Conductivity and the Thermodynamics of Micelle Formation of Sodium Perfluorooctanoate", Journal of Physical Chemistry, vol. 89, No. 21, Nov. 1, 1985, pp. 5308-5312.

Hisler, Kevin, et al., U.S. Appl. No. 17/251,328, entitled "Method for Producing 1-Chloro-3,3,3-Trifluoropropene," filed Dec. 11, 2020.

U.S. Appl. No. 17/053,250, Pigamo et al.

International Search Report (PCT/ISA/210) and Written Opinion (PCT/ISA/237), issued in PCT/FR2015/051653, dated Sep. 1, 2015, European Patent Office, Rijswijk, NL, 19 pages.

Wendlinger, Laurent, et al., U.S. Appl. No. 16/976,819, entitled "Process for the Production of 2,3,3,3-Tetrafluoropropene," filed Aug. 31, 2020.

Wendlinger, Laurent, et al., U.S. Appl. No. 16/976,599, entitled "Process for the Production of 2,3,3,3-Tetrafluoropropene," filed Aug. 28, 2020.

Pigamo, Anne, et al., U.S. Appl. No. 17/053,250 entitled "Method for Producing 1-Chloro-3,3,3-Trifluoropropene," filed Nov. 5, 2020.

International Search Report (PCT/ISA/210) and translation and Written Opinion (PCT/ISA/237) dated Jun. 26, 2019, by the European Patent Office as the International Searching Authority for International Application No. PCT/FR2019/050478.

U.S. Appl. No. 17/280,547, Boutier et al.

Boutier, Jean-Christophe, et al., et al., U.S. Appl. No. 17/280,547, entitled "Stabilization of 1-Chloro-3,3,3-Trifluoropropene," filed in the U.S. Patent and Trademark Office dated Mar. 26, 2021.

\* cited by examiner

PROCESS FOR PRODUCING 2-CHLORO-3,3,3-TRIFLUOROPROPENE

TECHNICAL FIELD OF THE INVENTION

The present invention relates to the production of hydrofluoroolefins. More particularly, the present invention relates to the production of 2-chloro-3,3,3-trifluoropropene.

Technological Background of the Invention

Halogenated hydrocarbons, in particular fluorinated hydrocarbons, such as hydrofluoroolefins, are compounds which have a structure of use as functional materials, solvents, refrigerants, inflation agents and monomers for functional polymers or starting materials for such monomers. Hydrofluoroolefins, such as 2,3,3,3-tetrafluoropropene (HFO-1234yf), are attracting attention because they offer a promising behavior as refrigerants having a low global warming potential.

Processes for the production of fluoroolefins are usually carried out in the presence of a starting substance, such as a chlorine-containing alkane or a chlorine-containing alkene, and in the presence of a fluorinating agent, such as hydrogen fluoride. These processes can be carried out in the gas phase or in the liquid phase, in the absence or not of a catalyst.

2-Chloro-3,3,3-trifluoropropene is known as an intermediate in the production of 2,3,3,3-tetrafluoropropene (HFO-1234yf) and as monomer component for various types of polymers. 2-Chloro-3,3,3-trifluoropropene can be obtained from a compound such as 1,1,2,3-tetrachloropropene, 2,3,3,3-tetrachloropropene or 1,1,1,2,3-pentachloropropane.

WO 2007/079431 discloses a process for the production of 2-chloro-3,3,3-trifluoropropene in the gas phase in the presence of hydrofluoric acid and of a chromium-based catalyst. WO 2012/052797 also discloses a process for the production of 2-chloro-3,3,3-trifluoropropene in the gas phase starting from 1,1,1,2,3-pentachloropropane in the presence of HF and of a mixed Ni—Cr catalyst.

There is still a need for more effective processes for the production of 2-chloro-3,3,3-trifluoropropene.

SUMMARY OF THE INVENTION

The present invention relates to a process for the production of 2-chloro-3,3,3-trifluoropropene comprising the stages of:

a) providing a stream A comprising at least one of the compounds selected from the group consisting of 2,3-dichloro-1,1,1-trifluoropropane, 1,1,1,2,3-pentachloropropane, 1,1,2,3-tetrachloropropene and 2,3,3,3-tetrachloropropene;

b) in a reactor, bringing said stream A into contact with HF in the presence or absence of a catalyst in order to produce a stream B comprising 2-chloro-3,3,3-trifluoropropene; characterized in that the electrical conductivity of said stream A provided in stage a) is less than 15 mS/cm.

The present process makes it possible to optimize and improve the production of 2-chloro-3,3,3-trifluoropropene. An electrical conductivity value of less than 15 mS/cm of the stream A before the implementation of the fluorination stage makes it possible to guarantee an optimal effectiveness of the reaction in terms of conversion and of selectivity. If a catalyst is present, such a value makes it possible to also guarantee an optimal effectiveness of the catalyst.

According to a preferred embodiment, stage b) is carried out in the gas phase in the presence or absence of a catalyst.

According to a preferred embodiment, stage b) is carried out in the liquid phase in the presence of a catalyst.

According to a preferred embodiment, the electrical conductivity of said stream A is less than 10 mS/cm.

According to a preferred embodiment, stage b) is carried out in the presence of a chromium-based catalyst; in particular, said catalyst comprises a chromium oxyfluoride or a chromium oxide or a chromium fluoride or a mixture of these.

According to a preferred embodiment, the catalyst is based on chromium and also comprises a cocatalyst selected from the group consisting of Ni, Zn, Co, Mn and Mg; preferably, the content of cocatalyst is between 0.01% and 10%, based on the total weight of the catalyst.

According to a preferred embodiment, the stream B comprises, besides 2-chloro-3,3,3-trifluoropropene, HCl, HF, 2,3,3,3-tetrafluoropropene, and possibly 2,3-dichloro-3,3-difluoropropene, 2,3,3-trichloro-3-fluoropropene and/or 1,1,1,2,2-pentafluoropropane.

According to a preferred embodiment, stage b) is carried out at a temperature of between 320° C. and 440° C.

According to a preferred embodiment, stage b) is carried out in the presence of hydrofluoric acid having an electrical conductivity of less than 10 mS/cm.

DETAILED DESCRIPTION OF THE PRESENT INVENTION

The present invention relates to a process for the production of 2-chloro-3,3,3-trifluoropropene comprising the stages:

a) providing a stream A comprising at least one of the compounds selected from the group consisting of 2,3-dichloro-1,1,1-trifluoropropane, 1,1,1,2,3-pentachloropropane, 1,1,2,3-tetrachloropropene and 2,3,3,3-tetrachloropropene;

b) in a reactor, bringing said stream A into contact with HF in the presence or absence of a catalyst in order to produce a stream B comprising 2-chloro-3,3,3-trifluoropropene.

According to a preferred embodiment, the electrical conductivity of said stream A provided in stage a) is less than 15 mS/cm. Advantageously, the electrical conductivity of said stream A provided in stage a) is less than 14 mS/cm, preferably less than 13 mS/cm, more preferentially less than 12 mS/cm, in particular less than 11 mS/cm, more particularly less than 10 mS/cm, favorably less than 9 mS/cm, advantageously favorably less than 8 mS/cm, preferentially favorably less than 7 mS/cm, more preferentially favorably less than 6 mS/cm, particularly favorably less than 5 mS/cm. The electrical conductivity is measured using an inductive conductivity measurement cell and according to the practice known to a person skilled in the art. The electrical conductivity is measured at ambient temperature. The electrical conductivity is measured at a pressure equal to the pressure at which stage b) is carried out. The electrical conductivity of the stream A can be reduced, in order to achieve a conductivity of less than 15 mS/cm, by reducing the concentration of electrolyte possibly present in the stream according to techniques known to a person skilled in the art (distillation, cooling and separation by settling, passing through 3 to 5 A molecular sieves or zeolites). Preferably, the measurement cell is coated with a material resistant to a corrosive medium, in particular resistant to hydrofluoric acid.

The electrical conductivity of said stream A is measured prior to stage b). Preferably, the electrical conductivity of said stream A is measured when the latter is in the liquid form. Said process according to the present invention can thus comprise a stage of heating and vaporization of said stream A prior to the implementation of stage b) in order to provide said stream A in the gaseous form. Preferably, said stream A employed in stage b) is in the gaseous form as it is brought into contact with HF.

According to a preferred embodiment, stage b) is carried out in the gas phase in the presence of a catalyst, preferably a chromium-based catalyst. Preferably, the chromium-based catalyst can be a chromium oxide (for example $CrO_2$, $CrO_3$ or $Cr_2O_3$), a chromium oxyfluoride or a chromium fluoride (for example $CrF_3$) or a mixture of these. The chromium oxyfluoride can contain a fluorine content of between 1% and 60% by weight, based on the total weight of the chromium oxyfluoride, advantageously between 5% and 55% by weight, preferably between 10% and 52% by weight, more preferentially between 15% and 52% by weight, in particular between 20% and 50% by weight, more particularly between 25% and 45% by weight, favorably between 30% and 45% by weight, more favorably from 35% to 45% by weight, of fluorine, based on the total weight of the chromium oxyfluoride. The catalyst can also comprise a cocatalyst chosen from the group consisting of Ni, Co, Zn, Mg, Mn, Fe, Zn, Ti, V, Zr, Mo, Ge, Sn, Pb and Sb; preferably Ni, Co, Zn, Mg and Mn; in particular Ni, Co and Zn. The content by weight of the cocatalyst is between 1% and 10% by weight, based on the total weight of the catalyst. The catalyst may or may not be supported. A support, such as alumina, activated alumina, aluminum halides ($AlF_3$, for example), aluminum oxyhalides, activated carbon, magnesium fluoride or graphite, can be used.

Preferably, the catalyst can have a specific surface between 70 and 225 $m^2/g$, advantageously between 90 and 200 $m^2/g$, preferably between 100 and 190 $m^2/g$, in particular between 125 and 180 $m^2/g$. Alternatively, the catalyst can have a specific surface between 1 and 100 $m^2/g$, preferably between 5 and 80 $m^2/g$, more preferentially between 5 and 70 $m^2/g$, ideally between 5 and 50 $m^2/g$, in particular between 10 and 50 $m^2/g$, more particularly between 15 and 45 $m^2/g$.

According to another preferred embodiment, stage b) is carried out in the gas phase in the absence of catalyst.

When stage b) is carried out in the gas phase, in the absence or in the presence of catalyst, the pressure at which stage b) is carried out can be atmospheric pressure or a pressure greater than atmospheric pressure; advantageously, the pressure at which stage b) is carried out can be greater than 1.5 bara, preferably greater than 2.0 bara, in particular greater than 2.5 bara, more particularly greater than 3.0 bara. Preferably, stage b) can be carried out at a pressure of between atmospheric pressure and 20 bara, preferably between 2 and 18 bara, more preferentially between 3 and 15 bara.

Preferably, in the gas phase, in the absence or in the presence of catalyst, stage b) of the present process is carried out with a contact time between 1 and 100 s, preferably between 2 and 75 s, in particular between 3 and 50 s. Preferably, the molar ratio between HF and said at least one of the compounds of said stream A, i.e. 2,3-dichloro-1,1,1-trifluoropropane, 1,1,1,2,3-pentachloropropane, 1,1,2,3-tetrachloropropene and 2,3,3,3-tetrachloropropene, can vary between 1:1 and 150:1, preferably between 2:1 and 125:1, more preferentially between 3:1 and 100:1. An oxidant, such as oxygen or chlorine, can be added during stage b). The molar ratio of the oxidant to the hydrocarbon compound can be between 0.005 and 2, preferably between 0.01 and 1.5.

The oxidant can be pure oxygen, air or a mixture of oxygen and nitrogen.

According to a preferred embodiment, in the gas phase, in the absence or in the presence of catalyst, stage b) is carried out at a temperature of between 320° C. and 440° C., advantageously between 320° C. and 420° C., preferably between 330° C. and 400° C., more preferentially between 330° C. and 390° C., in particular between 340° C. and 380° C.

According to a preferred embodiment, stage b) can be carried out in the liquid phase. Preferably, stage b) is carried out in the liquid phase and in the presence of a catalyst. The catalyst can be a Lewis acid, a catalyst containing a halide of a metal, in particular a halide of antimony, tin, tantalum, titanium, of a transition metal, such as molybdenum, niobium, iron, cesium, oxides of transition metals, halides of metals of Group IVb, halides of metals of group Vb, chromium fluoride, fluorinated chromium oxides or a mixture thereof. For example, the catalyst can be $SbCl_5$, $SbCl_3$, $TiCl_4$, $SnCl_4$, $TaCl_5$, $NbCl_5$, $TiCl_4$, $FeCl_3$, $MoCl_6$, CsCl, and the corresponding fluorinated compounds. The catalyst may contain an ionic liquid, as described for example in applications WO2008/149011 (in particular from page 4, line 1 to page 6, line 15, incorporated by reference) and WO01/81353, and also the reference "liquid-phase HF Fluorination", Multiphase Homogeneous Catalysis, Ed. Wiley-VCH, (2002), 535.

In the liquid phase, stage b) can be carried out at a temperature of between 30° C. and 200° C., advantageously between 40° C. and 170° C., preferably between 50° C. and 150° C. Preferably, the HF/starting products molar ratio can be from 0.5:1 to 50:1, advantageously from 3:1 to 20:1 and preferably from 5:1 to 15:1. The term "starting products" refers to said at least one of the compounds selected from the group consisting of 2,3-dichloro-1,1,1-trifluoropropane, 1,1,1,2,3-pentachloropropane, 1,1,2,3-tetrachloropropene and 2,3,3,3-tetrachloropropene.

According to a preferred embodiment, the stream A can be mixed with hydrofluoric acid prior to stage b). Thus, stage a) of the present process can comprise the stages:
    a1) providing a gas stream comprising hydrofluoric acid;
    a2) providing said stream A comprising at least one of the compounds selected from the group consisting of 2,3-dichloro-1,1,1-trifluoropropane, 1,1,1,2,3-pentachloropropane, 1,1,2,3-tetrachloropropene and 2,3,3,3-tetrachloropropene and having an electrical conductivity of less than 15 mS/cm;
    a3) spraying said stream A in order to form droplets with a mean diameter of less than 500 μm;
    a4) vaporizing said droplets produced in stage a3) by mixing with said gas stream provided in stage a1), the resulting mixture being a gaseous mixture.

The gaseous mixture thus produced in stage a4) is used in stage b) of the present process to make possible the production of 2-chloro-3,3,3-trifluoropropene.

The present process can thus comprise the stages of:
    a1) providing a gas stream comprising hydrofluoric acid;
    a2) providing said stream A comprising at least one of the compounds selected from the group consisting of 2,3-dichloro-1,1,1-trifluoropropane, 1,1,1,2,3-pentachloropropane, 1,1,2,3-tetrachloropropene and 2,3,3,3-tetrachloropropene and having an electrical conductivity of less than 15 mS/cm;
    a3) spraying said stream A in order to form droplets with a mean diameter of less than 500 μm;

a4) vaporizing said droplets produced in stage a3) by mixing with said gas stream provided in stage a1), the resulting mixture being a gaseous mixture;

b) in a reactor, bringing said gaseous mixture of stage a4) into contact with HF in the presence or absence of a catalyst in order to produce a stream B comprising 2-chloro-3,3,3-trifluoropropene.

According to a preferred embodiment, the stream B comprises, besides 2-chloro-3,3,3-trifluoropropene, HCl, HF and 2,3,3,3-tetrafluoropropene. The stream B can possibly comprise 2,3-dichloro-3,3-difluoropropene, 2,3,3-trichloro-3-fluoropropene and/or 1,1,1,2,2-pentafluoropropane.

According to a preferred embodiment, the stream B is purified, preferably by distillation, in order to form a first stream comprising 2,3,3,3-tetrafluoropropene, HCl and possibly 1,1,1,2,2-pentafluoropropane and a second stream comprising HF and 2-chloro-3,3,3-trifluoropropene and possibly 2,3-dichloro-3,3-difluoropropene and 2,3,3-trichloro-3-fluoropropene. In particular, the distillation can be carried out at a pressure of 2 to 6 bara, more particularly at a pressure of 3 to 5 bara. In particular, the temperature at the distillation column top is from −35° C. to 10° C., preferably from −20° C. to 0° C.

According to a preferred embodiment, said stream B obtained in stage b) is cooled prior to the abovementioned purification. In particular, said stream B obtained in stage b) is cooled to a temperature of less than 100° C., then distilled in order to form said first stream comprising 2,3,3,3-tetrafluoropropene, HCl and possibly 1,1,1,2,2-pentafluoropropane, and said second stream comprising HF and 2-chloro-3,3,3-trifluoropropene and possibly 2,3-dichloro-3,3-difluoropropene and 2,3,3-trichloro-3-fluoropropene; the temperature at the distillation column top is from −35° C. to 10° C. and the distillation is carried out at a pressure from 2 to 6 bara.

Said stream B can be cooled, before distillation, to a temperature of less than 95° C., advantageously of less than 90° C., preferably of less than 85° C., more preferentially of less than 80° C., in particular of less than 70° C., more particularly of less than 60° C., favorably of less than 55° C., advantageously favorably of less than 50° C., preferentially favorably of less than 40° C., more preferentially favorably of less than 30° C., particularly favorably of less than 25° C., more particularly favorably of less than 20° C. The cooling of the flow of products obtained to such temperatures can facilitate the subsequent distillation.

The cooling of said stream B can be carried out by virtue of one or a plurality of heat exchangers. The cooling of said stream B can be carried out by passing the latter through one, two, three, four, five, six, seven, eight, nine or ten heat exchangers; preferably, the number of heat exchangers is between 2 and 8, in particular between 3 and 7.

Said second stream comprising HF and 2-chloro-3,3,3-trifluoropropene and possibly 2,3-dichloro-3,3-difluoropropene and 2,3,3-trichloro-3-fluoropropene can be purified, preferably by distillation, in order to form a third stream comprising hydrofluoric acid and possibly 2,3-dichloro-3,3-difluoropropene and 2,3,3-trichloro-3-fluoropropene, and a fourth stream comprising at least 95% by weight of 2-chloro-3,3,3-trifluoropropene, preferably at least 98% by weight of 2-chloro-3,3,3-trifluoropropene, based on the total weight of said fourth stream.

The third stream comprising hydrofluoric acid and possibly 2,3-dichloro-3,3-difluoropropene and 2,3,3-trichloro-3-fluoropropene can be recycled in stage b) or in stage a1) of the present process. In this case, said third stream is mixed with hydrofluoric acid before being used in stage b) or in stage a1) of the present process.

According to a preferred embodiment, stage b) is carried out in the presence of hydrofluoric acid having an electrical conductivity of less than 10 mS/cm, preferably of less than 5 mS/cm. The electrical conductivity of the hydrofluoric acid can be measured prior to its use in stage b) or stage a1) of the present process. Preferably, the electrical conductivity of the hydrofluoric acid is measured prior to stage b) or stage a1) and the hydrofluoric acid is in the liquid form during the measurement. The process can also comprise a stage of heating and of vaporization of the hydrofluoric acid prior to the implementation of stage b) in order to provide hydrofluoric acid in the gaseous form. Preferably, the hydrofluoric acid is in the gaseous form during the operation of bringing into contact with said stream A.

According to a specific embodiment, the process can comprise the stages of:

a1) providing a gas stream comprising hydrofluoric acid having an electrical conductivity of less than 10 mS/cm;

a2) providing said stream A comprising at least one of the compounds selected from the group consisting of 2,3-dichloro-1,1,1-trifluoropropane, 1,1,1,2,3-pentachloropropane, 1,1,2,3-tetrachloropropene and 2,3,3,3-tetrachloropropene and having an electrical conductivity of less than 15 mS/cm;

a3) spraying said stream A in order to form droplets with a mean diameter of less than 500 µm;

a4) vaporizing said droplets produced in stage a3) by mixing with said gas stream provided in stage a1), the resulting mixture being a gaseous mixture;

b) in a reactor, bringing said gaseous mixture of stage a4) into contact with HF in the presence or absence of a catalyst in order to produce a stream B comprising 2-chloro-3,3,3-trifluoropropene.

Preferably, the process according to the present invention is carried out continuously. Preferably, the process according to the present invention is carried out in the gas phase.

Example

The fluorination of HCC-240db (1,1,1,2,3-pentachloropropane) to give HCFO-1233xf (2-chloro-3,3,3-trifluoropropene) is carried out in a multitubular reactor. The reactor contains a bulk catalyst based on chromium oxide. The catalyst is activated by a series of stages comprising drying, fluorination, treatment under air and fluorination with recycling. This multistage treatment makes it possible to render the catalytic solid active and selective.

The fluorination process is carried out following the following operating conditions:

an absolute pressure in the fluorination reactor of 5.5 bar absolute a molar ratio of the HF to the sum of the organic materials fed by the recycling loop of between 12 and 15 a contact time of between 11 and 13 seconds a constant temperature in the reactor of 350° C.

The process is carried out with a stream of HCC-240db having two different electrical conductivity values: 6 and 25 mS/cm. The run is halted when the conversion of 1,1,1,2,3-pentachloropropane is a less than 50%. The values obtained are taken up in table 1 below The electrical conductivity of the stream of HCC-240db is measured using a cell sold by Endress+Hauser and referenced under the term InduMax P CLS 50 coated with a polymer coating of perfluoroalkoxy (PFA) type resistant to a corrosive medium containing HF.

TABLE 1

| Example | Electrical conductivity (mS/cm) | Duration of the run to achieve a conversion <50% (h) |
|---|---|---|
| 1 | 6 | 460 |
| 2 (comp.) | 25 | 100 |

The results given in detail in table 1 demonstrate that a stream comprising HCC-240db and having an electrical conductivity of less than 15 mS/cm makes it possible to maintain a sufficiently high conversion for a significant period of time. This is because a conversion of greater than 50% can be maintained for more than 460 h (example 1). On the contrary, the conversion of HCC-240db falls strongly when the electrical conductivity is too high (example 2).

The invention claimed is:

1. A process for the production of 2-chloro-3,3,3-trifluoropropene comprising the stages of:
    a) providing a stream A comprising at least one of the compounds selected from the group consisting of 2,3-dichloro-1,1,1-trifluoropropane, 1,1,1,2,3-pentachloropropane, 1,1,2,3-tetrachloropropane and 2,3,3,3-tetrachloropropene;
    b) in a reactor, bringing said stream A into contact with HF in the presence or absence of a catalyst in order to produce a stream B comprising 2-chloro-3,3,3-trifluoropropene;

wherein the electrical conductivity of said stream A provided in stage a) is less than 15 mS/cm.

2. The process as claimed in claim 1, wherein stage b) is carried out in the gas phase in the presence or absence of a catalyst.

3. The process as claimed in claim 1, wherein stage b) is carried out in the liquid phase in the presence of a catalyst.

4. The process as claimed in claim 1, wherein the electrical conductivity of said stream A is less than 10 mS/cm.

5. The process as claimed in claim 1, wherein stage b) is carried out in the presence of a chromium-based catalyst.

6. The process as claimed in claim 5, wherein the catalyst is based on chromium and also comprises a cocatalyst selected from the group consisting of Ni, Zn, Co, Mn and Mg.

7. The process as claimed in claim 1, wherein the stream B comprises, besides 2-chloro-3,3,3-trifluoropropene, HCl, HF, 2,3,3,3-tetrafluoropropene, and optionally 2,3-dichloro-3,3-difluoropropene, 2,3,3-trichloro-3-fluoropropene and/or 1,1,1,2,2-pentafluoropropane.

8. The process as claimed in claim 1, wherein stage b) is carried out at a temperature of between 320° C. and 440° C.

9. The process as claimed in claim 1, wherein stage b) is carried out in the presence of hydrofluoric acid having an electrical conductivity of less than 10 mS/cm.

10. The process as claimed in claim 1, wherein the process further comprises a step of reducing the concentration of electrolytes in stream A until the electrical conductivity of stream A is less than 15 mS/cm.

* * * * *